United States Patent
Grabarnik et al.

(10) Patent No.: US 10,760,044 B2
(45) Date of Patent: Sep. 1, 2020

(54) CHLORELLA VULGARIS PLANKTON STRAIN FOR OBTAINING FOOD BIOMASS

(71) Applicant: Vladimir Efimovich Grabarnik, Moscow (RU)

(72) Inventors: Vladimir Efimovich Grabarnik, Moscow (RU); Nikolai Viktorovich Karelin, Tverskaya obl. (RU); Nikolai Ivanovich Bogdanov, Penzenskaya obl. (RU)

(73) Assignee: Vladimir Efimovich Grabarnik, Moscow (RU)

( * ) Notice: Subject to any disclaimer, the term of this patent is extended or adjusted under 35 U.S.C. 154(b) by 12 days.

(21) Appl. No.: 16/053,888

(22) Filed: Aug. 3, 2018

(65) Prior Publication Data

US 2018/0346870 A1    Dec. 6, 2018

Related U.S. Application Data

(63) Continuation of application No. PCT/RU2018/000180, filed on Mar. 22, 2018.

(51) Int. Cl.
C12N 1/12    (2006.01)
C12R 1/89    (2006.01)

(52) U.S. Cl.
CPC .................. *C12N 1/12* (2013.01); *C12R 1/89* (2013.01); *C12N 2500/20* (2013.01)

(58) Field of Classification Search
None
See application file for complete search history.

(56) References Cited

FOREIGN PATENT DOCUMENTS

JP    2006101795 A  *  4/2006
RU    1751981 A1        2/1997

OTHER PUBLICATIONS

Bisova ("Cell-cycle regulation in green algae dividing by multiple fission" Journal of Experimental Botany, 2014, vol. 65, No. 10, 2585-2602). (Year: 2014).*
Bogdanov N.I. Suspenziya khlorelly v ratsione selskokhozyaistvennykh zhivotnykh, 2-e izdanie, ispravlennoe i dopolnennoe, Volgograd, 2007, pp. 1-48, retrieved from the Internet: www.bionex.pro.
Thomas Allnut F. C. et al. Characterization of Iron Uptake from Ferrioxamine B by Chlorella vulgaris. Plant Physiol., 1987, vol. 85, pp. 746-750.
International Search Report (English Translation) for PCT/RU2018/000180 dated May 31, 2018.

* cited by examiner

*Primary Examiner* — Robert J Yamasaki
*Assistant Examiner* — Charles Zoltan Constantine
(74) *Attorney, Agent, or Firm* — Millman IP Inc.

(57) ABSTRACT

The invention relates to biotechnology. The plankton strain of the unicellular green alga *Chlorella vulgaris* GKO, which has a thin cell wall, deposited in the Russian National Collection of Industrial Microorganisms under the registration number of VKPM A1-24. The strain VKPM A1-24 of the unicellular green alga *Chlorella vulgaris* can be used to produce food biomass intended for preparation of a beverage, concentrate, paste or dry powder. The invention makes it possible to shorten the period of cultivation of the biomass of unicellular algae.

2 Claims, No Drawings

CHLORELLA VULGARIS PLANKTON STRAIN FOR OBTAINING FOOD BIOMASS

CROSS-REFERENCE TO RELATED APPLICATIONS

This application is a continuation of, and claims the benefit of PCT/RU2018/000180, filed on Mar. 22, 2018, which claims the benefit of Russian Application No. 2017111369, filed on Apr. 5, 2017, the contents of which are incorporated herein by reference in their entirety

APPLICATION AREA

The invention relates to biotechnology and provides a novel plankton strain of the unicellular green alga *Chlorella vulgaris* for obtaining food biomass.

PRIOR ART

The typical strain 132-1 of *Chlorella vulgaris* f. *suboblonga* is known. The cells are ellipsoidal, 2.8-6.1 µm long and 1.7-5.5 µm wide, 8.0 µm and 5.5 µm on autospore formation, respectively. The cell wall is thin. The chloroplast is wide waist-like unclosed or trough-shaped. The chloroplast can be oriented longitudinally or transversely with respect to the long axis of the cell. The number of autospores is 2-4, less often is 8, and they are incorrectly ellipsoidal just after release. The typical strain 132-1 is stored in the Botanical Institute of the Russian Academy of Sciences and is a museum sample (V. M. Andreyeva, The genus *Chlorella*. Morphology, Systematics, and Classification Principles, Leningrad, Nauka Press, 1975.-110 p.).

The strain (prototype) of the unicellular green alga *Chlorella vulgaris* IFR No. C-111, intended for obtaining biomass and meeting the requirements of industrial cultivation (patent RU 1,751,981) is known. The cell membrane consists of the inner and outer layers, the outer layer containing an extensive myofibrillar material.

The disadvantages of the strain *Chlorella vulgaris* IFR No. C-111 are a stable asynchronous cycle of cell development, a strong and relatively thick cell membrane, as well as a long period of cultivation (four days).

DISCLOSURE OF THE INVENTION

The aim of the present invention is to provide a new plankton strain of microalgae for producing food biomass to be used as a food product in the form of a beverage, concentrate, paste or dry powder.

The technical result of the present invention is the preparation of a microalgae strain having a thin wall and capable of actively producing biomass in a synchronous cultivation mode on a modified nutrient medium with the incorporation of a carbon dioxide solution obtained using a grain material (naked oats) therein, reducing the cultivation time down to one day, for which *chlorella* passes through two life cycles, which allows it to gain the normative optical density of the suspension within 1.8-2.0 D (440).

DESCRIPTION OF THE INVENTION

The strain, initial for selection of *Chlorella vulgaris* GKO, deposited in the Russian National Collection of Industrial Microorganisms under the registration number of VKPM A1-24, on Feb. 7, 2017, was the strain *Chlorella vulgaris* IFR No. C-111 from the collection of the Institute of Plant Physiology of the Russian Academy of Sciences, Leninskiy Prospekt, 14, Moscow, Russia, 119991, which was cultivated on a nutrient medium with the inclusion of grain material (naked oats) to produce a carbon dioxide solution. A complete taxonomic description of the strain is: The strain *Ch. vulgaris* IGF No. C-111 was isolated from water samples of the Nurek reservoir (Tajikistan) in 1977. Morphological signs: Young cells are weakly ellipsoid, ranging in size from 1.5 to 2.0 µm. Adult cells are spherical, 6-8 µm in diameter on a liquid nutrient medium, do not settle to the bottom, and vessel walls do not overgrow. Round, smooth and convex colonies with smooth edges are formed on an agarized nutrient medium under light on the 7-10$^{th}$ day. The diameter of the colonies is 3-4 mm; they are stained dark green, the cell size being 5-8 µm. The chloroplast is broadgangly open. Physiological signs. It is divided into 2-8, very rarely into 16 autospores. The strain is autotrophic. To achieve a synchronous culture, an automatic device was used (patent RU 2,540,011).

As a result of the selection, a strain with a thin wall was selected, capable of reproducing biomass intensely in a synchronous mode of cultivation and maintaining the monoculture in the production process.

Morphological signs. The cells are ellipsoidal, especially young ones, 2.5 µm long and 1.6 µm wide, the adult cells are 5.4 µm long and 4.2 µm wide, with the formation of autospores up to 7.0 µm long and 5.2 µm wide. The cell wall is thin. The chloroplast is trough-shaped, its position relative to the long axis of the cell may be longitudinal or transverse. With the transverse arrangement of the chloroplast, it has the appearance of an unclosed girdle, while both ends of the cell remain free; it may line only one end of the cell. The pyrenoid is broadly ellipsoidal, the starch wrap consists of two hemispherical shells. Usually no nucleus in living cells is visible. The number of autospores is 2 and less often 4, immediately after release they have an ellipsoidal shape. The number of spores is always even. The empty shell of the maternal cell has one rupture. On the agarized mineral medium, convex, smooth, shiny colonies with smooth margins are formed in the light on the seventh day. The diameter of the colonies is 1-2 mm, they are dark green, the cells are 4.8 µm long and 4.0 µm wide. The color of the cells, both young and adult, is dark green.

Physiological signs. The strain is autotrophic, under laboratory conditions it grows on a modified mineral nutrient medium, which includes a carbon dioxide solution, prepared on the basis of naked oats. The composition of the nutrient medium (1) is as follows:

1. Ammonium nitrate, GOST 2-2013—0.18 g.
2. Ammophos, GOST 18918-85, 15% solution—0.09 ml.
3. Potassium sulfate, GOST 4145-74, 12% solution—0.33 ml.
4. Iron chloride, GOST 4147-74, 1% solution—0.15 ml.
5. Cobalt nitrate, GOST 4528-78, 0.01% solution—0.5 ml.
6. Copper sulfate, GOST 4165-78, 0.01% solution—0.5 ml.
7. Carbon dioxide, solution (pH 3-5)—2.0-5.0 ml.
8. Tap water according to SanPiN (Russian sanitary rules and regulations) 2.1.4.1074-01—1,000 ml.

In production conditions, a working nutrient medium is used, which consists of solutions of four chemical reagents and a carbon dioxide solution prepared on naked oats. The composition of the working nutrient medium (2) per 1 liter of tap water according to SanPiN 2.1.4.1074-01 is as follows:

1. Nitrogen-phosphoric solution—0.25 ml.
2. Iron-sodium solution—0.15 ml.
3. Copper-cobalt solution—0.15 ml.
4. Potassium sulfate solution—0.30 ml.
5. Carbon dioxide solution (pH 3-5)—2.0-5.0 ml.

The strain requires no constant mixing, no feeding of balloon carbon dioxide and no air bubbling through the culture.

The use of the carbon dioxide solution prepared for naked oats for *chlorella* cultivation promotes maintaining $CO_2$ in the suspension during the growth of the algae and the formation of bacterial-algic microbiocenosis, which greatly accelerates the course of biological processes in the aquaculture ecosystem.

Lighting of the culture of the strain is made by DNaT (an arched sodium tubular lamp) or DRI-250 (an arched mercury lamp with radiating additives) lamps. Given that both solar and artificial lighting can be used, the daily rhythm consists of two phases, light and dark, with different periods of illumination. The first phase is 20 hours, the second one is 4 hours, and the light load includes two equal periods of 10 hours. After the first light period (the stage of photosynthesis), the lamp lighting is switched off for 4 hours to execute the dark phase regime—the stage of spore formation and their release from the maternal cell. Given that the culture operates in a synchronous mode, it needs at least 4 hours for sporulation and cell division. During the dark phase, the autospores are released and emerge from the cells into the culture, where they are ready for further growth. Then, the lamps are switched on for 10 hours to execute the second period of the light phase. Thus, *chlorella* passes through two life cycles during one day, which allows it to gain the normative optical density of cells.

Under both sunlight and artificial illumination, the optimal culture temperature during the light phase of 28-30° C., both lowering the temperature below 28° C. and rising it above 30° C. leads to a delay in cell growth in the culture. In the dark phase, the temperature may drop down to 23-25° C.

Cultural properties. The strain is planktonic, and its cells possess the properties inherent in these algae, i.e. they are in a suspended state and freely float in the water bulk, they are characterized by a uniform distribution in the culture medium, which is facilitated by the presence of a negative cell charge.

The strain is cultivated all year round, there are no seasonal changes, during cultivation it suppresses pathogenic microflora, yeast, fungi and viruses, no agglutination occurs, no cell autolysis is observed, any alkaloids are absent.

The strain is grown under the conditions of a monoculture, it strictly observes these conditions with respect to other algae and has immunity to phages.

Biotechnological properties and cultivation features. For the strain cultivation, a plant for the cultivation of plankton algae and a lamp for the plant for growing plankton algae (patent RU 2,540,011) is used, which allows both artificial and solar illumination. The plant contains a system of *chlorella* bioreactors, a carbon dioxide solution reactor, a nutrient solution preparation station, a light source in the form of electric lamps, equipped with a cooling system. The filling, regulating, washing and draining devices are located and connected under the bioreactor section system. The containers for the nutrient solution preparation and for collection and storage of the ready suspension are connected to the aquariums by pipelines. The plant allows providing the *chlorella* suspension production process in an automatic mode. The optimum cultivation conditions, which are maintained in the plant, allow obtaining the normative optical density of the suspension within 1.8-2.0 D for one day (440). The strain cultivation is conducted in compliance with the requirements of sanitation, however, no creation of sterility conditions is required.

The cells in the culture are sensitive to dynamic impacts and die by mechanical mixing of the culture in plants with electric pumps, as well as by bubbling air or carbon dioxide through the culture. In any plant where *chlorella* is cultivated, no contact of the suspension with metallic objects is allowed, the pipelines in the installation must have food certification. The strain cultivation is carried out with strict adherence to the biotechnology of growing *chlorella*.

The cultivation of the plankton strain *Chlorella vulgaris* GKO using a carbon dioxide solution prepared on the basis of naked oats, promotes the production of food biomass and excludes constant mixing of the suspension, without feeding balloon carbon dioxide or bubbling air through it.

Example of Obtaining Food Biomass

The working nutrient medium (2) and the mother culture of the plankton strain *Chlorella vulgaris* GKO with an optical density of 1.8-2.0 D (440) are introduced into the aquariums of the plant (patent RU 2,540,011) in a ratio of 1:1. The lighting is turned on for 10 hours. During the cultivation, the temperature of the suspension in the aquariums is maintained within 28-30° C. After this period, the lamps are switched off for 4 hours. At the end of these 4 hours, the lamps are turned on for 10 hours.

At the end of the second light period, the culture is drained and used as food biomass to prepare beverages, concentrates, paste or dry powder. The biomass is 1.0 g/L dry weight for a daily period of the cultivation.

The following materials illustrate the achievement of the goal. Food biomass was obtained in the automatic plant (patent RU 2,540,011) using the plankton strain *Chlorella vulgaris* GKO in the synchronous cultivation process on the working nutrient medium (2), which reached the normative value of optical density of 1.8-2.0 in one day D (440).

The microalgae strain *Chlorella vulgaris* GKO has successfully passed the stage of laboratory, experimental, pilot and industrial cultivation and is currently used for the preparation of food products.

Thus, a novel plankton strain of the *Chlorella vulgaris* GKO microalgae with a thin wall has been obtained, capable of actively producing biomass in a synchronous cultivation mode on a modified nutrient medium with the inclusion of a carbon dioxide solution prepared with the use of grain material (naked oats), it is intended for the preparation food biomass, which can be used to make beverages, concentrates, paste or dry powder.

The invention claimed is:
1. *Chlorella vulgaris* strain VKPM AI-24.
2. A food biomass comprising *Chlorella vulgaris* strain VKPM AI-24.

* * * * *